(12) United States Patent
Sugaya

(10) Patent No.: US 11,100,642 B2
(45) Date of Patent: Aug. 24, 2021

(54) COMPUTER SYSTEM, AND METHOD AND PROGRAM FOR DIAGNOSING ANIMALS

(71) Applicant: OPTIM CORPORATION, Saga (JP)

(72) Inventor: Shunji Sugaya, Tokyo (JP)

(73) Assignee: OPTIM CORPORATION, Saga (JP)

(*) Notice: Subject to any disclaimer, the term of this patent is extended or adjusted under 35 U.S.C. 154(b) by 100 days.

(21) Appl. No.: 16/492,462

(22) PCT Filed: Oct. 31, 2016

(86) PCT No.: PCT/JP2016/082302
§ 371 (c)(1),
(2) Date: Sep. 9, 2019

(87) PCT Pub. No.: WO2018/078867
PCT Pub. Date: May 3, 2018

(65) Prior Publication Data
US 2020/0380678 A1     Dec. 3, 2020

(51) Int. Cl.
*G06K 9/00* (2006.01)
*G06T 7/00* (2017.01)
(Continued)

(52) U.S. Cl.
CPC ............ *G06T 7/0014* (2013.01); *A01K 29/00* (2013.01); *A61B 5/0077* (2013.01);
(Continued)

(58) Field of Classification Search
None
See application file for complete search history.

(56) References Cited

U.S. PATENT DOCUMENTS

2016/0073614 A1\* 3/2016 Lampe ................. A61B 5/1128
600/408

FOREIGN PATENT DOCUMENTS

JP    2003-228701 A    8/2003
JP    2003-339648 A    12/2003
(Continued)

OTHER PUBLICATIONS

Sathiyabarathi ("Infrared thermography: A potential noninvasive tool to monitor udder health status in dairy cows" Veterinary World, 9(10): 1075-1081, Published online: Oct. 15, 2016) (Year: 2016).\*
(Continued)

*Primary Examiner* — Wei Wen Yang
(74) *Attorney, Agent, or Firm* — Norton Rose Fulbright US LLP; James R. Crawford

(57) ABSTRACT

The purpose of the present disclosure is to provide a computer system, an animal diagnosis method, and a program in which the accuracy of animal diagnosis can be improved. The computer system acquires a visible light image of an animal imaged by a camera, compares the acquired visible light image with a normal visible light image of the animal and performs image analysis, identifies a species of the animal according to the result of the image analysis, identifies an abnormal portion of the animal according to the result of the image analysis, acquires environmental data of the animal, and diagnoses a condition of the animal according to the identified species, the identified abnormal portion and the acquired environmental data.

3 Claims, 8 Drawing Sheets

(51) Int. Cl.
*G06T 7/11* (2017.01)
*G06T 7/174* (2017.01)
*A01K 29/00* (2006.01)
*A61B 5/00* (2006.01)

(52) U.S. Cl.
CPC ............ *G06K 9/00362* (2013.01); *G06T 7/11* (2017.01); *G06T 7/174* (2017.01); *A61B 2503/40* (2013.01); *A61B 2576/00* (2013.01); *G06T 2207/10048* (2013.01)

(56) References Cited

FOREIGN PATENT DOCUMENTS

| | | |
|---|---|---|
| JP | 2006-084425 A | 2/2006 |
| WO | 2006-064635 A1 | 6/2006 |
| WO | 2015-060376 A1 | 4/2015 |

OTHER PUBLICATIONS

International Search Report issued in PCT/JP2016/082302 dated Dec. 27, 2016.

\* cited by examiner

Diagnosis Database

| Animal | Classi-fication | Date | Type of feed | Amount of feed | Amount of water | Body temperature | ... | Step count | Diagnosis |
|---|---|---|---|---|---|---|---|---|---|
| Cow | Hols-tein | 2nd July | Thick feed | Normal | 2 liter | 38°C | ... | 120 step | — |
| | | 11th November | Thick feed | None | Almost none | 37°C | ... | 550 step | In pregnancy |
| | | ... | ... | ... | ... | ... | ... | ... | ... |
| | | ... | ... | ... | ... | ... | ... | ... | ... |
| | Gue-rnsey | ... | ... | ... | ... | ... | ... | ... | ... |
| | | ... | ... | ... | ... | ... | ... | ... | ... |
| | | ... | ... | ... | ... | ... | ... | ... | ... |

Fig. 10

COMPUTER SYSTEM, AND METHOD AND PROGRAM FOR DIAGNOSING ANIMALS

This application is a 371 of International Patent Application No. PCT/JP2016/082302 filed on Oct. 31, 2016, which is incorporated herein by reference in its entirety.

TECHNICAL FIELD

The present disclosure relates to a computer system, an animal diagnosis method and program that diagnosis an animal based on an image.

BACKGROUND ART

In recent years, in the field of livestock farming and the like, it is performed to diagnose whether an abnormality occurs in livestock based on an image acquired by imaging the livestock.

The diagnosis of the livestock is performed by imaging an image such as a moving image or a still image of the livestock, and analyzing the imaged image.

As a system for diagnosing the livestock, a configuration is disclosed in which a lameness diagnosis is performed by imaging a walking motion of a horse and analyzing an image of the captured walking motion (see Patent Document 1).

CITATION LIST

Patent Document

Patent Document 1: JP-A-2003-228701

SUMMARY

Technical Problem

However, in the configuration of Patent Document 1, the diagnosis is performed according to the walking motion, thus, it is difficult to discriminate from the walking motion, and it is difficult to diagnose the condition of the animal (for example, whether the animal is pregnant, whether a predetermined site is sick).

The purpose of the present disclosure is to provide a computer system, an animal diagnosis method, and a program in which the accuracy of animal diagnosis can be improved.

Solution to Problem

The present disclosure provides the following solutions.

The present disclosure provides a computer system including a first image acquisition unit configured to acquire a visible light image of an animal imaged by a camera, an image analysis unit configured to compare the acquired visible light image with a normal visible light image of the animal and perform image analysis, an animal identifying unit configured to identify a species of the animal according to the result of the image analysis, an abnormal portion identifying unit configured to identify an abnormal portion of the animal according to the result of the image analysis, an environmental data acquisition unit configured to acquire environmental data of the animal, and a first diagnosis unit configured to diagnose a condition of the animal based on the identified species, the identified abnormal portion and the acquired environmental data.

According to the present disclosure, the computer system acquires a visible light image of an animal imaged by a camera, compares the acquired visible light image with a normal visible light image of the animal and performs image analysis, identifies the species of the animal according to the result of the image analysis, identifies an abnormal portion of the animal according to the result of the image analysis, acquires environmental data of the animal, and diagnoses a condition of the animal according to the identified species, the identified abnormal portion and the acquired environmental data.

The present disclosure is a category of computer system, and exerts the same function/effect according to the category even in other categories such as an animal diagnosis method and program.

Advantageous Effects of Invention

According to the present disclosure, it is capable of providing a computer system, an animal diagnosis method, and a program in which the accuracy of animal diagnosis can be improved.

BRIEF DESCRIPTION OF DRAWINGS

FIG. 10 is a diagram illustrating an example of a diagnosis database stored in the computer 10.

DESCRIPTION OF EMBODIMENTS

Hereinafter, the best aspect for carrying out the present disclosure will be described with reference to the drawings. Note that, this is merely an example, and the technical scope of the present disclosure is not limited to this.

Outline of Animal Diagnosis System 1

Figure 1:
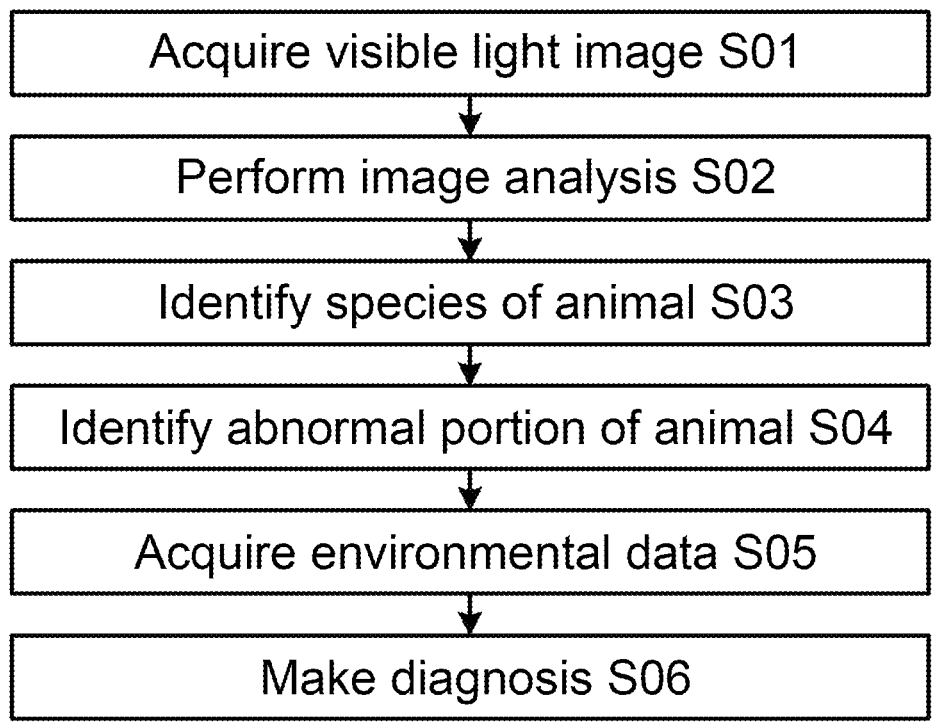
FIG. 1 is a diagram illustrating an outline of an animal diagnosis system 1.

Based on FIG. 1, an outline of a suitable embodiment of the present disclosure will be described. FIG. 1 is a diagram for explaining the outline of an animal diagnosis system 1 according to a suitable embodiment of the present disclosure. The animal diagnosis system 1 includes a computer 10, acquires an image obtained by imaging an animal, and diagnoses the condition of the animal.

The computer 10 is a computing device communicably connected to a camera such as a visible light camera or an infrared camera, a sensor, and the like (not illustrated). The animal diagnosis system 1 acquires a visible light image from a visible light camera, acquires an infrared image from an infrared camera, and acquires, from a sensor, at least one environmental data among a group including a date when the visible light image and the infrared image were acquired, type and amount of feed given before the date, amount of water given before the date, and body temperature of the animal.

First, the computer 10 acquires a visible light image imaged by a camera that is not illustrated (step S01). The computer 10 acquires the visible light image such as a moving image or a still image of the animal imaged by the visible light camera.

Note that, in addition to the visible light image, the computer 10 may acquire the infrared image such as a moving image, a still image of the animal imaged by the infrared camera. At this time, the visible light camera and the infrared camera may be realized by the same imaging device, or the visible light camera and the infrared camera may image the same target by arranging the visible light camera and the infrared camera in parallel or in the vicinity. That is, the visible light camera and the infrared camera take images of the same object from substantially the same imaging point.

The computer 10 analyzes the acquired visible light image in comparison with a normal visible light image of the animal (step S02). The computer 10 compares the feature value and the color of the visible light image with the feature value and the color of the normal visible light image of the animal. The computer 10 compares a plurality of the feature values and the colors of the normal visible light images of the animal with the feature values and the colors of the acquired visible light image. Various kinds of information for identifying an animal, such as the species or the name of the animal, are associated with the feature values and the colors of the normal visible light image of the animal.

Note that, the computer 10 may compare temperatures in addition to the feature values and the colors of the acquired visible light image. In this case, the computer 10 may acquire the infrared image in addition to the visible light image, extract the temperature of the infrared image, and compare the extracted temperature with the temperature of a normal infrared image of the animal.

The computer 10 identifies the species of the animal as the result of the image analysis (step S03). By performing the image analysis described above, the computer 10 identifies the feature value and the color of the normal visible light image of the animal coincident with the feature value or the color of the visible light image acquired this time, and identifies the species of the animal associated with the identified visible light image as the species of the animal present in the visible light image acquired this time. At this time, the computer 10 identifies the feature value or the color of the normal visible light image of the animal, which is similar to or coincident with the feature value or the color of the acquired visible light image.

The computer 10 identifies an abnormal portion of the animal as the result of the image analysis (step S04). The computer 10 identifies a portion having a feature value or a color different from the normal condition of the animal among the feature values or the colors of the acquired visible light image by the image analysis described above as an abnormal portion.

Note that, the computer 10 may identify the abnormal portion of the animal based on the temperature of the acquired infrared image described above. In this case, the computer 10 may compare the extracted temperature with the temperature of the normal infrared image of the animal, and identify a portion in which the temperature is abnormal based on whether the temperature difference is within a predetermined range, or whether the temperature is coincident with a reference temperature, and the like.

The computer 10 acquires environmental data in which the animal is located (step S05). The computer 10 acquires at least one environmental data related to the living environment of the animal among a group including date when the visible light image was acquired, type and amount of feed given before the date, amount of water given before the date, and body temperature of the animal.

The computer 10 diagnoses the condition of the animal from the identified the species of the animal, the identified abnormal portion, and the acquired environmental data (step S06). The computer 10 diagnoses the condition of the animal by referring to a diagnosis database in which the species of the animal, the abnormal portion, the environmental data, and the diagnosis result are associated in advance. The computer 10 executes the diagnosis of the animal by extracting the diagnosis result, which is associated with the species of the animal identified this time, the identified abnormal portion, and the acquired environmental data, from the diagnosis database.

The above is the outline of the animal diagnosis system 1.

System Configuration of Animal Diagnosis System 1

Figure 2:
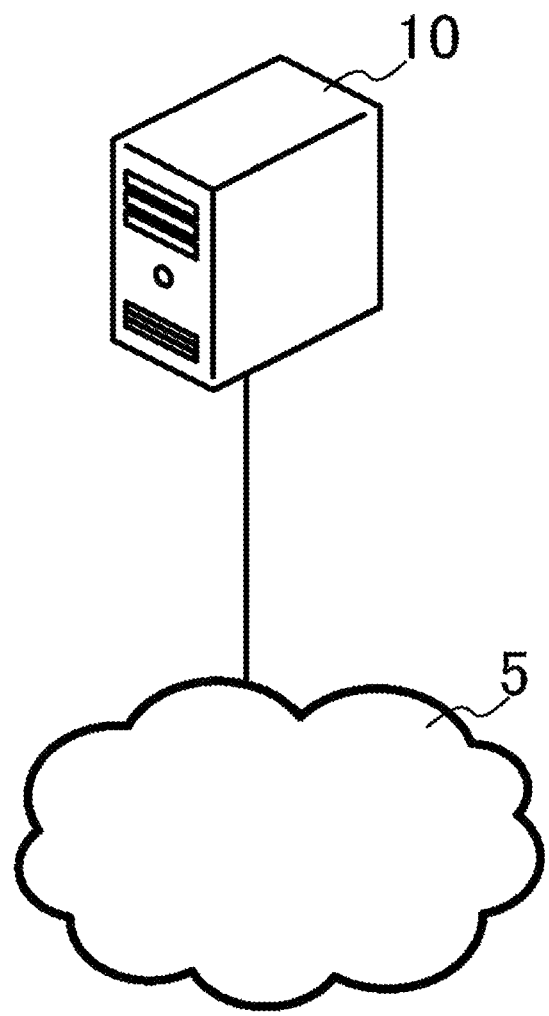
FIG. 2 is an overall configuration diagram of the animal diagnosis system 1.

Based on FIG. 2, a system configuration of the animal diagnosis system 1 according to a suitable embodiment of the present disclosure will be described. FIG. 2 is a diagram illustrating the system configuration of the animal diagnosis system 1 according to the suitable embodiment of the present disclosure. The animal diagnosis system 1 includes a computer 10 and a public network (the Internet, the third and fourth generation communication networks, etc.) 5, acquires an image obtained by imaging an animal, and diagnoses the animal.

The animal diagnostic system 1 is connected to cameras such as a visible light camera configured to image an visible light image such as a moving image and a still image of the animal or an infrared camera configured to image an infrared image such as a moving image and a still image of the animal, and sensors configured to detect at least one environmental data, which is related to the living environment of the animal, among the group including the date when the visible light image was acquired, the type and the amount of feed given before the date, the amount of water given before the date, and the body temperature of the animal, such that data communication is possible. The computer 10 acquires various data from these devices.

The computer 10 is the above-described computing device having functions to be described later.

Description of Each Function

Figure 3:
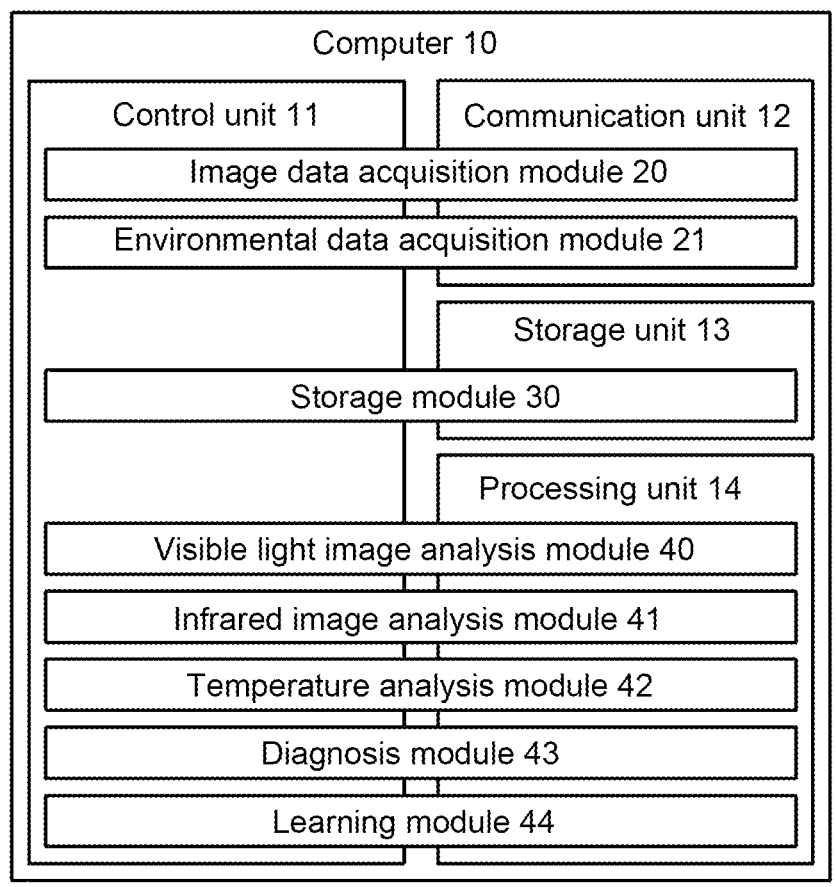
FIG. 3 is a functional block diagram of a computer 10.

Based on FIG. 3, the functions of the animal diagnosis system 1 according to a suitable embodiment of the present disclosure will be described. FIG. 3 is a functional block diagram of the computer 10.

The computer 10 includes a central processing unit (CPU), a random access memory (RAM), a read only memory (ROM), and the like as a control unit 11, and a device enabling communication with other devices (cameras, sensors) as a communication unit 12, for example, a WiFi (Wireless Fidelity) compliant device construed under IEEE802.11. Further, the computer 10 includes a data storage unit such as a hard disk, a semiconductor memory, a recording medium, a memory card, and the like, as a storage unit 13. The storage unit 13 stores various databases described later. Further, the computer 10 includes a device and the like configured to execute various processes such as image processing and condition diagnosis as a processing unit 14.

In the computer 10, the control unit 11 reads a predetermined program in cooperation with the communication unit 12 to realize an image data acquisition module 20, and an environmental data acquisition module 21. Further, in the computer 10, the control unit 11 reads a predetermined program in cooperation with the storage unit 13 to realize a storage module 30. Further, in the computer 10, the control unit 11 reads a predetermined program in cooperation with the processing unit 14 to realize a visible light image analysis module 40, an infrared image analysis module 41, a temperature analysis module 42, a diagnosis module 43, and a learning module 44.

Animal Diagnosis Process

Figure 4:
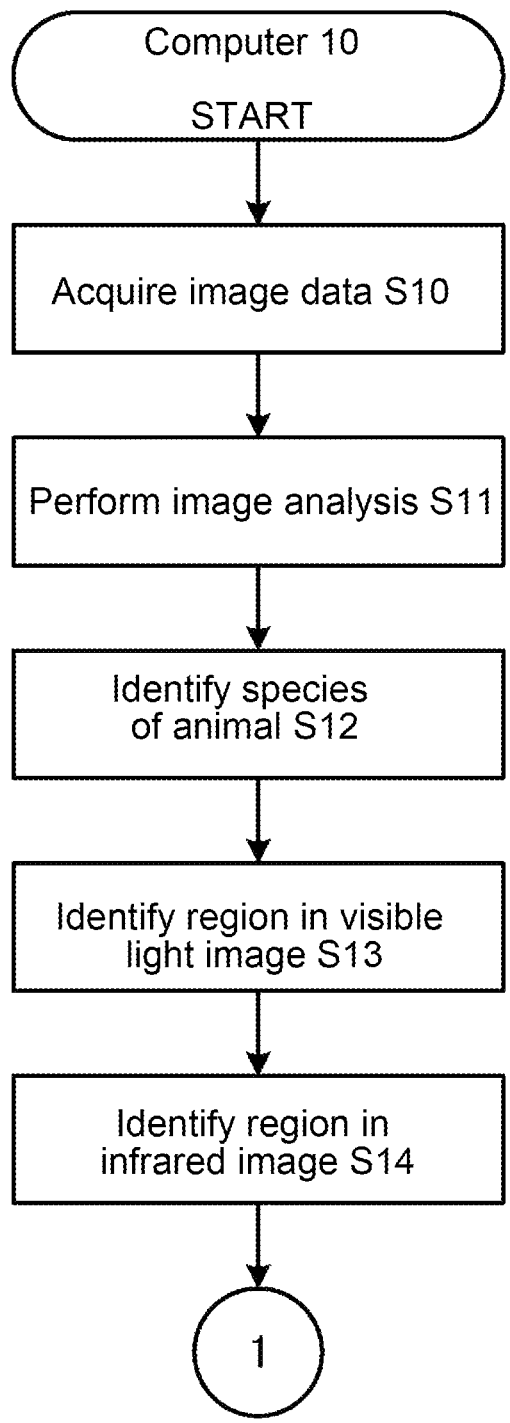
FIG. 4 is a flowchart illustrating an animal diagnosis process executed by the computer 10.
Figure 5:
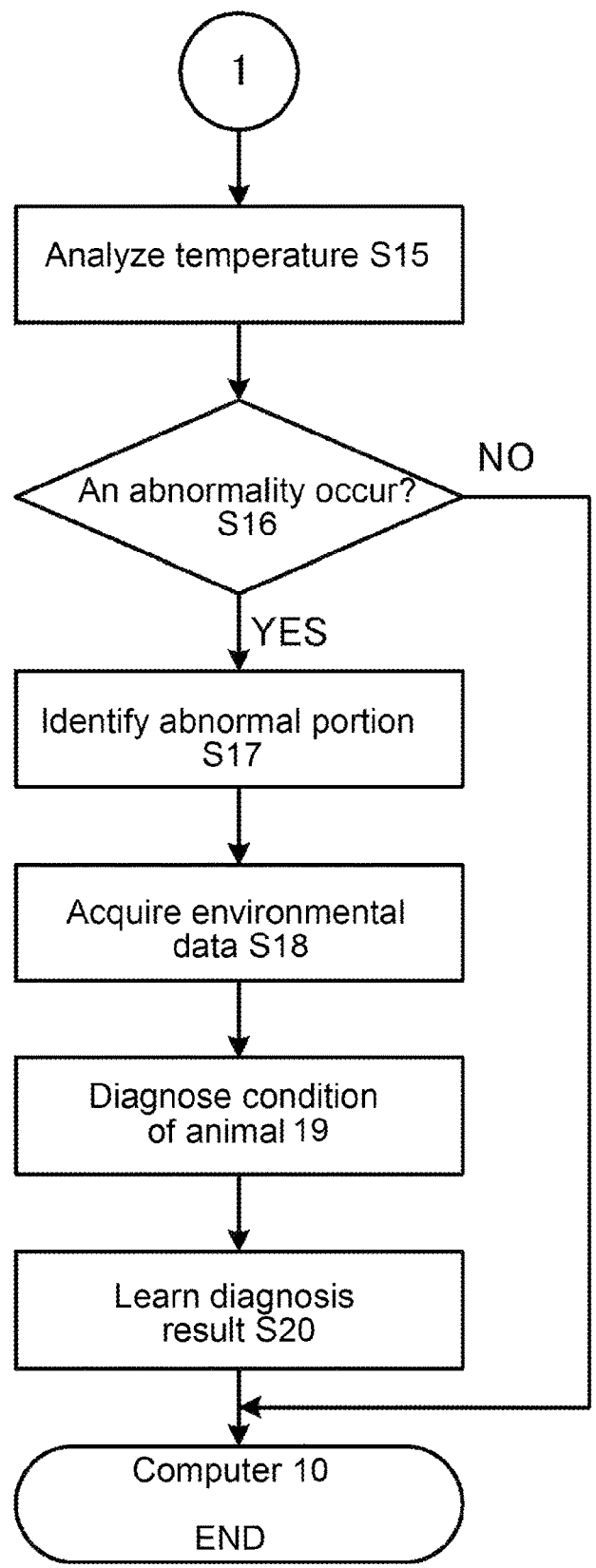
FIG. 5 is a flowchart illustrating the animal diagnosis process executed by the computer 10.

Based on FIG. 4 and FIG. 5, an animal diagnosis process executed by the animal diagnosis system 1 will be described. FIG. 4 and FIG. 5 are flowcharts illustrating the animal diagnosis process executed by the computer 10. The process executed by each module described above will be described together with this processing. In the following description, the animal diagnostic system 1 will be described as a system configured to diagnose a cow as an animal.

First, the image data acquisition module 20 acquires image data of the visible light image and the infrared image of the animal (step S10). In step S10, the image data acquisition module 20 acquires visible light image data that is the visible light image imaged by the visible light camera. Further, the image data acquisition module 20 acquires infrared image data that is the infrared image imaged by the infrared camera. The image data acquisition module 20 acquires the image data at a plurality of time points such as at predetermined time intervals or at preset times. The image data acquired by the image data acquisition module 20 are imaged from the same imaging point and are image data obtained by imaging the same target. Note that, in the following description, it is assumed that the computer 10 diagnoses the animal based on the image data at a predetermined time point.

Note that, the image data acquisition module 20 may acquire only visible light image data. In this case, the animal diagnosis process may be executed without the process using the infrared image data described later.

Figure 6:
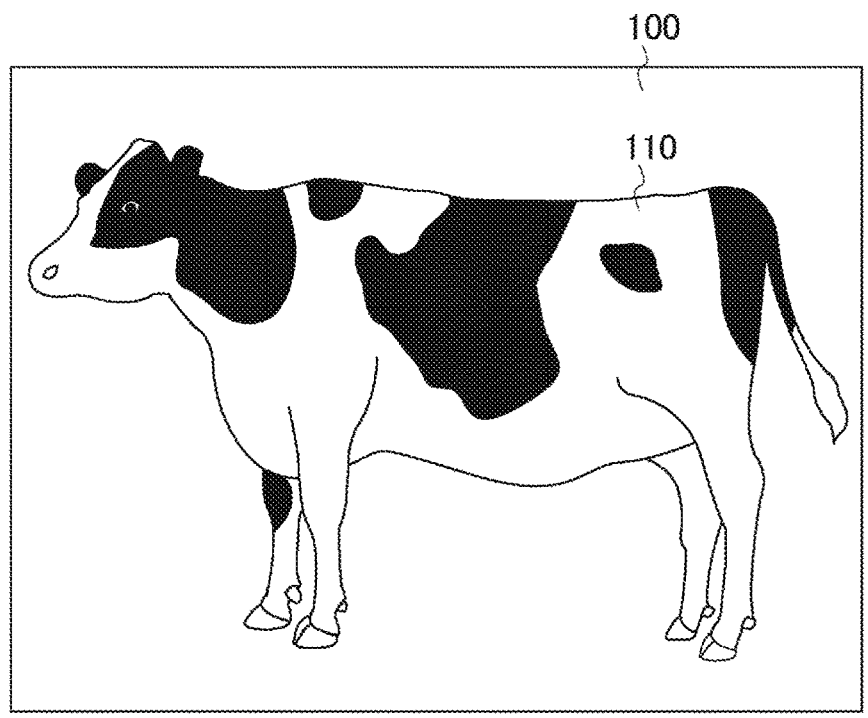
FIG. 6 is a diagram schematically illustrating an example of visible light image data acquired by the computer 10.

Based on FIG. 6, the visible light image data of the animal acquired by the image data acquisition module 20 will be described. FIG. 6 is a diagram schematically illustrating an example of the visible light image data of the animal acquired by the image data acquisition module 20. In FIG. 6, the image data acquisition module 20 acquires a visible light image 100 indicating the visible light image data. In the visible light image 100, an animal 110 is reflected. Note that, landscape, natural object, artificial object other than the animal 110 may be reflected in the visible light image 100, but are omitted for simplification of the description. Further, a plurality of the animals 110 or animal of different species from the animal 110 may be reflected in the visible light image 100.

Figure 7:
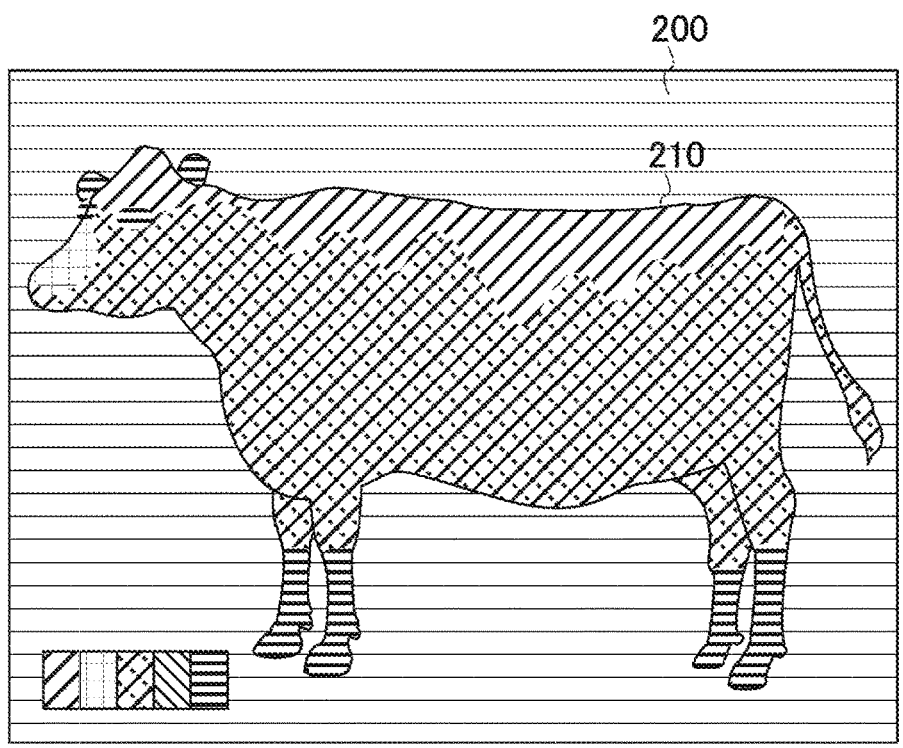
FIG. 7 is a diagram schematically illustrating an example of infrared image data acquired by the computer 10.

Based on FIG. 7, the infrared image data of the animal acquired by the image data acquisition module 20 will be described. FIG. 7 is a diagram schematically illustrating an example of the infrared image data of the animal acquired by the image data acquisition module 20. In FIG. 7, the image data acquisition module 20 acquires an infrared image 200 indicating the infrared image data. In the infrared image 200, an animal 210 is reflected. In the infrared image 200, each temperature is indicated by hatching for convenience. Note that, landscape, natural object, artificial object other than the animal 210, may be reflected in the infrared image 200, but are omitted for simplification of the description. Further, a plurality of the animals 210 or animal of different species from the animal 210 may be reflected in the infrared image 200.

The visible light image analysis module 40 analyzes the acquired visible light image data (step S11). In step S11, the visible light image analysis module 40 compares the acquired visible light image with a visible light image of a normal condition of the animal stored in advance in the storage module 30. The visible light image of the normal condition of the animal is an image that is imaged a part or the entire animal site such as head, nose, shoulder, buttock, perianal area, stomach area, and leg, in a healthy condition by a visible light camera for each species or each individual of the animal. The storage module 30 associates and stores various kinds of information for identifying animals such as species and individuals in the visible light image of the normal condition of the animals. The visible light image analysis module 40 extracts the feature value such as the shape and size of each site and the color of each site of the acquired visible light image. Further, the visible light image analysis module 40 extracts the feature value and the color of each site of the visible light image stored in the storage module 30. The visible light image analysis module 40 compares the feature value and the color extracted from the acquired visible light image with the feature value and the color extracted from the stored visible light image.

The visible light image analysis module 40 recognizes the shape of the animal present in the visible light image by executing edge analysis or the like on the acquired visible light image. Further, the visible light image analysis module 40 recognizes the shape of the animal present in the visible light image by executing edge analysis or the like on the visible light image stored in the storage module 30. The visible light image analysis module 40 compares these shapes. Further, the visible light image analysis module 40 recognizes the RGB values of the visible light image by executing color extraction or the like on the acquired visible light image. Further, the visible light image analysis module 40 recognizes the RGB values of the visible light image by executing color extraction or the like on the visible light image stored in the storage module 30. The visible light image analysis module 40 compares these RGB values.

The visible light image analysis module 40 identifies the species of the animal based on the result of the image analysis (step S12). In step S12, a stored visible light image having coincident or similar feature value or color is identified based on the feature value and the color extracted from the acquired visible light image. The visible light image analysis module 40 acquires various kinds of information for identifying the animal associated with the visible light image.

Note that, when a plurality of animal individuals are recognized in the visible light image, the visible light image analysis module 40 executes process of step S11 and step S12 described above with respect to each individual to identify the species of each individual.

Further, the computer 10 may identify the species of the animal based on the acquired infrared image. In this case, by comparing the temperature of each site in the acquired infrared image with the temperature of each site in the infrared image of the normal condition of the animal stored in the storage module 30, the computer 10 identifies the stored infrared image having coincident or similar temperature with respect to the temperature recognized from the acquired infrared image, and identifies the species of the animal associated to the identified infrared image. The computer 10 may execute this process for each individual when a plurality of animal individuals present in the infrared image. Further, the computer 10 may identify the species of the animal based on both the acquired visible light image and the infrared image. In this case, the process for the visible light image and the process for the infrared image that are executed by the computer 10 described above may be executed in combination.

The visible light image analysis module 40 identifies, in the visible light image, a plurality of regions corresponding to a plurality of predetermined sites of the animal respectively. In step S13, the predetermined site is, for example, a part of the structure such as head, nose, shoulder, buttock, perianal area, stomach area, leg, or a preset site. The visible light image analysis module 40 recognizes, in the visible light image, the position of a part of the structure or a preset site according to the feature value, and identifies the recognized position as a region corresponding to the predetermined site. Further, the visible light image analysis module 40 recognizes, in the visible light image, the position of a part of the structure or a preset site according to the color, and identifies the recognized position as a region corresponding to the predetermined site. The visible light image analysis module 40 identifies a plurality of regions corresponding to the plurality of predetermined sites respectively.

Figure 8:
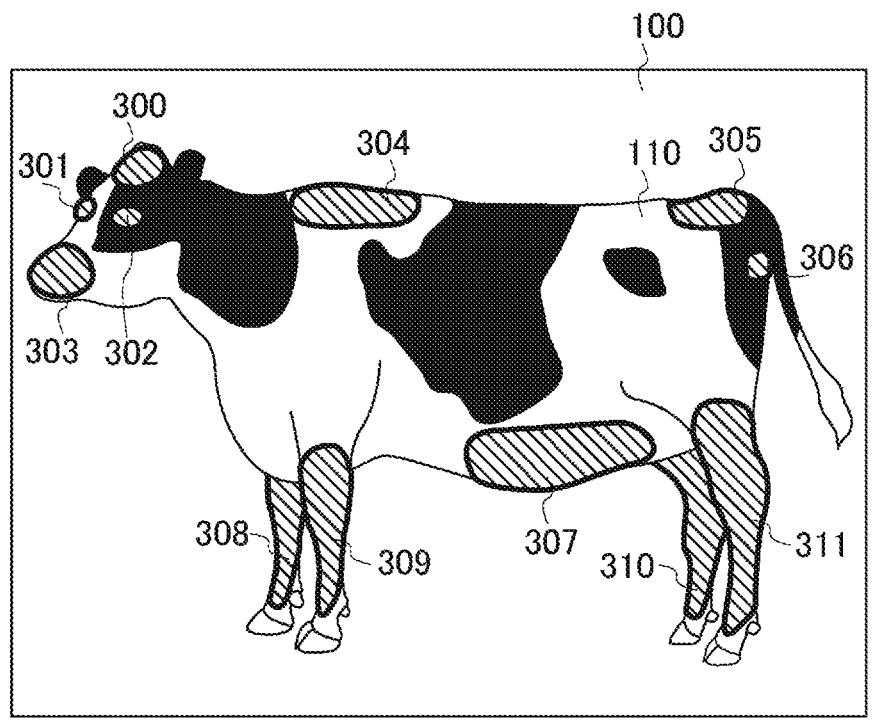
FIG. 8 is a diagram schematically illustrating an example of a state in which the computer 10 identifies a predetermined site in a visible light image.

Based on FIG. 8, the region corresponding to the predetermined site that the visible light image-analysis module 40 identifies is described. FIG. 8 is a diagram schematically illustrating an example of a state in which the visible light image analysis module 40 identifies a predetermined site. In FIG. 8, based on the feature value and the color, the visible light image analysis module 40 identifies regions in the visible light image 100 in which the predetermined sites of head, nose, shoulder, buttock, perianal area, stomach area and leg are located. That is, the visible light image analysis module 40 identifies the regions corresponding to sites of head sections 300 to 302, nose 303, shoulder 304, buttock 305, perianal area 306, stomach area 307, and legs 308 to 311 of the animal 110. In FIG. 8, the identified regions are indicated by hatching for convenience. Although the region refers to a part of each site, it may refer to the entire corresponding site. Note that, the number, types and positions of the sites to be identified can be changed appropriately.

Note that, when a plurality of animal individuals are recognized in the visible light image, the visible light image analysis module 40 may execute this process for each individual. Further, the visible light image analysis module 40 may recognize each individual and recognize the positional relationship of each individual. The positional relationship may be recognized based on the distance from the imaging point, the coordinates in the visible light image, and the like.

The infrared image analysis module 41 identifies a region in the infrared image corresponding to the identified region in the visible light image (step S14). In step S14, the infrared image analysis module 41 identifies the region of the infrared image corresponding to the identified region of each site of the animal by comparing the visible light image with the infrared image. The infrared image analysis module 41 acquires the position of the region in the visible light image as coordinates, and identifies a position coincident with the acquired coordinates as the region in the infrared image corresponding to the identified region in the visible light image.

Figure 9:
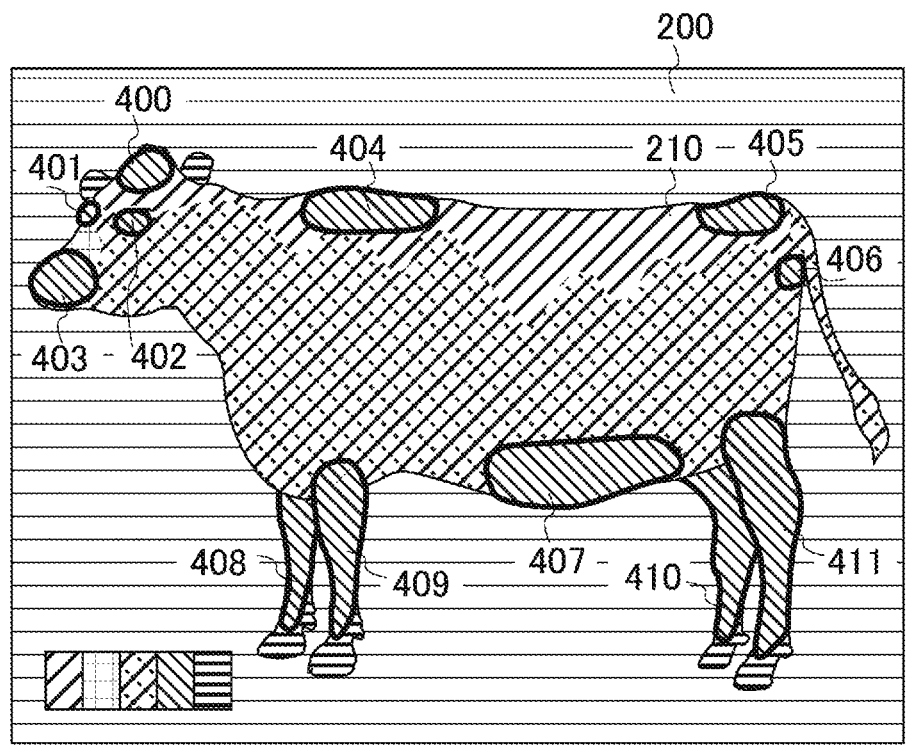
FIG. 9 is a diagram schematically illustrating an example of a state in which the computer 10 identifies a region in an infrared image.

Based on FIG. 9, the region in the infrared image corresponding to the region in the visible light image that the infrared image analysis module 41 identifies will be described. FIG. 9 is a diagram schematically illustrating an example of a state in which the infrared image analysis module 41 identifies the region in the infrared image. In FIG. 9, regions in the infrared image 200 corresponding to the sites of the head sections 300 to 302, the nose 303, the shoulder 304, the buttock 305, the perianal area 306, the stomach area 307, and the legs 308 to 311 of the identified animal 110 in the visible light image 100 described above is identified. It is identified by comparing the position in the visible light image 100 with the position in the infrared image 200. The infrared image analysis module 41 acquires the position coordinates of each site in the visible light image 100, and identifies the position in the infrared image corresponding to the acquired position coordinates as the region in the infrared image corresponding to the region in the visible light image. The infrared image analysis module 41 identifies sites of head sections 400 to 402, nose 403, shoulder 404, buttock 405, perianal area 406, stomach area 407, and legs 408 to 411 of the animal 210. In FIG. 9, the identified regions are indicated by hatching for convenience. The region refers to a part or the entire site depending on the identified site in the visible light image described above. Note that, the number, types and positions of the sites can be appropriately changed according to the visible light image.

The temperature analysis module 42 analyzes the temperature of the identified region in the infrared image (step S15). In step S15, the temperature analysis module 42 acquires the temperature of each region and identifies the temperature of each region, based on the infrared image.

The diagnosis module 43 diagnoses the animal and determines whether abnormality occurs, based on the temperature of the identified region in the infrared image (step S16). In step S16, the diagnosis module 43 diagnoses the animal based on the acquired temperature of each region. The diagnosis module 43 diagnoses the animal based on a reference temperature that is a temperature in a normal condition of the animal corresponding to each site and is stored in the storage module 30. The diagnosis module 43 calculates the temperature difference between the temperature of the identified region in the infrared image and the reference temperature that the region corresponds, and determines whether the calculated temperature difference is within a predetermined range (for example, within 0.5° C., within 1° C., within 2° C., etc.). The diagnosis module 43 determines that no abnormality occurs when it is determined that the temperature difference is within the predetermined range, and determines that an abnormality occurs when it is determined that the temperature difference is not within the predetermined range.

Note that, the diagnosis module 43 may diagnose the animal by a method other than the diagnosis based on the reference temperature described above. For example, the animal may be diagnosed according to only the temperature of the region in the identified infrared image, otherwise, when a plurality of animal individuals present, the animal may be diagnosed based on the positional relationship of each individual or the temperature of each individual. Further, the animal may be diagnosed by combining a plurality of methods. For example, the diagnosis module 43 determines an abnormality occurs when the temperature of the identified region in the infrared image is identified to be an abnormal temperature (step S16). Further, the diagnosis module 43 compares, in the identified infrared image, the temperature of the region of a first individual with the temperature of the region of a second individual, calculates the temperature difference between them, and diagnoses that an abnormality occurs in any one or both of the first individual and the second individual.

Further, the diagnosis module 43 diagnoses the animal based on one visible light image data and one infrared image data, and may diagnose the animal based on either or both of a plurality of visible light images and a plurality of infrared images acquired within a predetermined period. In this case, the diagnosis module 43 may diagnose the animal based on change amount, change width or the change itself of the feature value, the color, the temperature of the individuals acquired from any one or both of the visible light image and the infrared image. Further, the diagnosis module 43 may diagnose the animal based on the average value of the temperatures of the individuals acquired from the plurality of infrared images. That is, the diagnosis module 43 may calculate the temperature difference between the average value of the temperatures and the reference temperature by comparing the average value of the temperatures of the individual or each site with the reference temperature, and may diagnose the animal based on whether the temperature difference is within a predetermined range. Further, the diagnosis module 43 may diagnose the animal by a method other than these methods.

Further, the diagnosis module 43 may diagnose the animal based only on the visible light image without using the infrared image. In this case, the diagnostic module 43 determines whether an abnormality occurs by comparing the feature value, the color, and the like of each site or a preset site present in the visible light image, which are extracted by the visible light image analysis module 40, with the feature value, the color, and the like of the identified species of the animal.

In step S16, when the diagnosis module 43 determines that no abnormality occurs in the individual (step S16 NO), the process ends. Note that, in step S16, the computer 10 may transmit a notification indicating that no abnormality occurs in the animal to an external terminal or the like (not illustrated). The external terminal may notify the user the instruction by displaying the notification on a display unit of the external terminal or playing the notification by voice.

On the other hand, when the diagnosis module 43 determines in step S16 that an abnormality occurs (step S16 YES), the diagnosis module 43 identifies an abnormal portion of the animal that is a site where the abnormality of the animal occurs (step S17). In step S17, the diagnostic module 43 identifies the abnormal portion based on any one or both of the feature value or color of each site extracted from the visible light image and the temperature of each site identified from the infrared image. The diagnostic module 43 identifies a site where the feature value and the color of each extracted site are different from the feature value and the color of the normal condition of the animal as the abnormal portion. Further, the diagnostic module 43 identifies a portion where the temperature of each identified site is different from the temperature of the normal condition of the animal as the abnormal portion.

The environmental data acquisition module 21 acquires environmental data indicating the living environment of the animal (step S18). In step S18, the environmental data acquisition module 21 acquires at least one data among the group including the date when the visible light image was acquired, the type and the amount of feed given before the date, the amount of water given before the date, and the body temperature of the animal, as the environmental data. The environmental data acquisition module 21 acquires the environmental data from sensors (not illustrated) such as a clock, a meteorological instrument, a rain gauge, a rain and snow meter, a thermometer, a wind direction anemometer, a hygrometer, a barometer, an actinometer, a pyrheliometer, a visibility meter, a pedometer, a weight scale, and a terminal device configured to accept input of necessary information. These sensors are disposed adjacent the animal or adjacent a place where the animal is planted.

Note that, the environmental data acquisition module 21 may acquire the environmental data at other timings. For example, the environmental data acquisition module 21 may acquire the environmental data at the same time as acquiring image data of the animal, or may acquire the environmental data after identifying the species of the animal. That is, the environmental data acquisition module 21 may acquire environmental data prior to diagnosing the condition of the animal. Further, the sensors may be sensors detecting environmental information other than the example described above. Further, the disposed position of the sensors can be appropriately changed into a position where the living environment of the animal not only the example described above can be detected.

The diagnosis module 43 diagnoses the condition of the animal from the identified species, the identified abnormal portion, and the acquired environmental data (step S19). In step S19, the diagnosis module 43 determines the condition of the animal based on the diagnosis database that is stored in the storage module 30 and associates the species of the animal, the abnormal portion of the animal, the environmental data of the animal, and the diagnosis result. The diagnostic module 43 identifies the position corresponding to the combination of the species identified this time, the identified abnormal portion, and the acquired environmental data by referring to the diagnosis database. The diagnosis module 43 extracts the diagnosis result corresponding to the position. The diagnosis module 43 diagnoses the extracted diagnosis result as the condition of the animal.

Note that, the diagnosis module 43 diagnoses the condition of the animal from any one or more of the combination of the identified species, the identified abnormal portion, and the acquired environmental data. In this case, when extracting a plurality of corresponding diagnosis results, the diagnosis module 43 may calculate the probability for each diagnosis result based on the information. For example, when a plurality of diagnosis results are acquired in the identified abnormal portion, the diagnosis module 43 calculates the probability of each diagnosis result based on the matching rate of the environmental data. Further, when a plurality of diagnosis results are acquired in the acquired environmental data, the diagnostic module 43 may set weightings in advance to each data of the environmental data, and may calculate the probability for each diagnosis result by associating the weighting with the probability. Further, the diagnosis module 43 may calculate the probability by a method other than these methods.

Diagnosis Database

Based on FIG. 10, the diagnosis database stored in the storage module 30 will be described. FIG. 10 is a diagram illustrating an example of the diagnosis database stored in the storage module 30. In FIG. 10, the storage module 30 associates and stores information for identifying an animal such as animal, classification, environmental data indicating a living environment of the animal such as date, type of feed, amount of feed, amount of water, body temperature, and step count, and the information indicating the diagnosis result. The animal refers to a species of animal. The classification refers to animal breed. The date refers to the date when the visible light image was acquired. The species of feed refers to the content of the feed given to the animal before the date when the visible light image was acquired last time. The amount of feed refers to the amount of the feed given to the animal before the date when the visible light image was acquired last time, or the amount of feed actually consumed by the animal. The amount of water refers to the amount of the water given to the animal before the date when the visible light image was acquired last time, or the amount of water actually consumed by the animal. The body temperature refers to the current body temperature of the animal. The step count is the number of steps of the animal between the date when the visible light image was acquired last time and the date when the visible light image was acquired this time. The diagnosis refers to the condition of the animal when in these conditions. In the diagnosis database, the case where the animal is in the normal condition and the case where an abnormality occurs are associated with each other for each breed. When the animal is in a normal condition, the storage module 30 associates and stores the fact that the diagnosis result is that no abnormality occurs. When an abnormality occurs in the animal, the storage module 30 associates and stores the content that respectively corresponds to the diagnosis result.

Note that, in the diagnosis database, the information for identifying the animal, the information for indicating the environmental data and the diagnosis result are not limited to the examples described above, and other information may be added, otherwise, some of the items described above may be deleted. Further, the number of species and classifications of the animal is not limited to the example described above, and may be at least more than this. Further, the diagnosis database may be generated for each animal and each classification.

The diagnosis module 44 learns the diagnosis result (step S20). In step S20, the learning module 44 learns the diagnosis result using the environment data and the visible light image or the infrared image as the feature values. That is, the environmental data and a pair of an image and a diagnosis result in the diagnostic database stored in the storage module 30 are learned as "supervised data" to generate diagnosis determination data. The storage module 30 stores the generated diagnosis determination data, and the diagnostic module 43 determines the diagnosis result based on the diagnostic determination data learned this time when acquiring a new image.

The above is the animal diagnosis process.

The units and functions described above are realized by the computer (including a CPU, an information processing device, and various terminals) reading and executing a predetermined program. The program is provided, for example, in the form provided from the computer via a network (SaaS: software as a service). Further, the program is provided, for example, in a form of being recorded on a computer-readable recording medium such as a flexible disk, a CD (such as a CD-ROM), and a DVD (such as a DVD-ROM, a DVD-RAM). In this case, the computer reads the program from the recording medium, transfers the program to an internal storage device or an external storage device, stores and executes it. Further, the program may be recorded in advance in a storage device (recording medium) such as a magnetic disk, an optical disk, and a magneto-optical disk, and may be provided from the storage device to the computer via a communication line.

The embodiments of the present disclosure have been described above, but the present disclosure is not limited to these embodiments described above. Further, the effects described in the embodiments of the present disclosure only list the most suitable effects resulting from the present disclosure, and the effects of the present disclosure are not limited to the effects described in the embodiments of the present disclosure.

REFERENCE SIGNS LIST

1 Animal diagnosis system; 10 Computer

What is claimed is:

1. A computer system, comprising:
an image acquisition unit configured to acquire a visible light image and an infrared image of an animal imaged by a camera;
an image analysis unit configured to compare the acquired visible light image with a visible light image of the animal stored in advance in a storage unit and perform image analysis;
an animal identifying unit configured to identify a species of the animal according to the result of the image analysis;
a first image processing unit configured to identify, by comparing at least one feature value extracted from the acquired visible light image with at least one feature value extracted from the stored visible light image, a region, in the visible light image, which corresponds to each of a plurality of predetermined sites of the animal;
a second image processing unit configured to identify a region, in the infrared image, which corresponds to each identified region in the visible light image;
an abnormal portion identifying unit configured to identify an abnormal portion of the animal according to the temperature of the identified region in the infrared image;
an environmental data acquisition unit configured to acquire environmental data of the animal; and
a first diagnosis unit configured to diagnose, by referring to a diagnosis database, a condition of the animal based on the identified species, the temperature of the identified abnormal portion and the acquired environmental data,
wherein the diagnosis database is configured to store a correspondence between the condition of the animal and a combination of the identified species, the temperature of the identified abnormal portion and the acquired environmental data in advance, and
wherein the environmental data acquisition unit acquires at least one environmental data among a group including a date when the visible light image was acquired, type and amount of feed given before the date, amount of water given before the date, and body temperature of the animal.

2. An animal diagnosis method executed by a computer system, comprising:
acquiring a visible light image and an infrared image of an animal imaged by a camera;
comparing the acquired visible light image with a visible light image of the animal stored in advance in a storage unit and performing image analysis;
identifying a species of the animal according to the result of the image analysis;
identifying, by comparing at least one feature value extracted from the acquired visible light image with at least one feature value extracted from the stored visible light image, a region, in the visible light image, which corresponds to each of a plurality of predetermined sites of the animal;

identifying a region, in the infrared image, which corresponds to each identified region in the visible light image;

identifying an abnormal portion of the animal according to the temperature of the identified region in the infrared image;

acquiring environmental data of the animal; and diagnosing, by referring to a diagnosis database, a condition of the animal according to the identified species, the temperature of the identified abnormal portion and the acquired environmental data, wherein the diagnosis database is configured to store a correspondence between the condition of the animal and a combination of the identified species, the temperature of the identified abnormal portion and the acquired environmental data in advance, and wherein the environmental data acquisition unit acquires at least one environmental data among a group including a date when the visible light image was acquired, type and amount of feed given before the date, amount of water given before the date, and body temperature of the animal.

3. A non-transitory computer readable storage medium, storing a computer readable program causing a computer system to execute:

acquiring a visible light image and an infrared image of an animal imaged by a camera;

comparing the acquired visible light image with a visible light image of the animal stored in advance in a storage unit and performing image analysis;

identifying a species of the animal according to the result of the image analysis;

identifying, by comparing at least one feature value extracted from the acquired visible light image with at least one feature value extracted from the stored visible light image, a region, in the visible light image, which corresponds to each of a plurality of predetermined sites of the animal;

identifying a region, in the infrared image, which corresponds to each identified region in the visible light image;

identifying an abnormal portion of the animal according to the temperature of the identified region in the infrared image;

acquiring environmental data of the animal; and diagnosing, by referring to a diagnosis database, a condition of the animal according to the identified species, the temperature of the identified abnormal portion and the acquired environmental data, wherein the diagnosis database is configured to store a correspondence between the condition of the animal and a combination of the identified species, the temperature of the identified abnormal portion and the acquired environmental data in advance, and wherein the environmental data acquisition unit acquires at least one environmental data among a group including a date when the visible light image was acquired, type and amount of feed given before the date, amount of water given before the date, and body temperature of the animal.

* * * * *